United States Patent [19]

Miura et al.

[11] Patent Number: 5,093,267
[45] Date of Patent: Mar. 3, 1992

[54] METHOD FOR BIOCHEMICAL ASSAY AND AN ANALYZER FOR THE METHOD

[75] Inventors: Junkichi Miura, Hitachi; Mamoru Taki, Ibaraki; Yoshio Watanabe; Masao Kamahori, both of Hitachi; Hiroyuki Miyagi, Mito, all of Japan

[73] Assignee: Hitachi, Ltd., Tokyo, Japan

[21] Appl. No.: 267,293

[22] Filed: Nov. 4, 1988

[30] Foreign Application Priority Data

Nov. 11, 1987 [JP] Japan .................. 62-283322

[51] Int. Cl.⁵ .......................................... G01N 33/00
[52] U.S. Cl. .................. 436/93; 210/656; 210/198.2; 73/61.1 C; 436/111; 436/131; 436/161; 436/178
[58] Field of Search ............ 210/635, 656, 198.2; 436/161, 93, 111, 131, 161, 178; 73/61.1 C

[56] References Cited

U.S. PATENT DOCUMENTS

| 3,657,118 | 4/1972 | Kraffczyk et al. | 210/658 |
| 3,825,410 | 7/1974 | Bagshawe | 436/57 |
| 3,888,629 | 6/1975 | Bagshawe | 436/541 |
| 4,705,757 | 11/1987 | Ohkura | 436/111 |
| 4,767,529 | 8/1988 | Boos et al. | 210/502.1 |

OTHER PUBLICATIONS

ANALYSIS, Feb. 1987, pp. 100-105.
High Performance Liquid Chromatographic Analysis of Amino Acids in Physiological Fluids: On-Line Precolumn Derivatization with o-Phthaldialdehyde, Nestle Research Department CH-1814, Switzerland 133, pp. 330-335 (1983).
J. Chromatogr. Library, 32, pp.435-447 (1985) "Miniaturization of High Performance Liquid Chromatography" (Micro-HPLC) M. Verzele and C. Dewaele.
Journal of Chromatography, vol. 303, pp. 238-243, R. H. Buck and K. Krummen, "High-Performance liquid chromatography with automated pre-column derivatization for amino acids".

Primary Examiner—Ivars Cintins
Assistant Examiner—Cynthia L. Nessler
Attorney, Agent, or Firm—Antonelli, Terry, Stout & Kraus

[57] ABSTRACT

Catecholamines can be detected with high sensitivity in a shortened time period, by introducing a sample containing catecholamines into an adsorption column packed with an adsorbent to adsorb catecholamines to the column, then introducing a reagent for derivatization to effect pre-column labeling and then analyzing the pre-column labeled catecholamines by means of high performance liquid chromatography. Connection of the adsorption column and a separation column of high performance liquid chromatography via a fluid path changeover valve enables to automated analysis of catecholamines.

15 Claims, 4 Drawing Sheets

METHOD FOR BIOCHEMICAL ASSAY AND AN ANALYZER FOR THE METHOD

BACKGROUND OF THE INVENTION

1. FIELD OF THE INVENTION

The present invention relates to a method for biochemical assay and an analyzer used for the method. More particularly, the present invention relates to a method for biochemical assay which comprises converting objective components into appropriate derivatives, separating the derivatives into respective components and assaying the components and to an analyzer used for the method.

2. STATEMENT OF THE PRIOR ART

In analysis of biochemical components by means of liquid chromatography, the objective components are often present in a trace amount and hence, some methods have been hitherto provided for purposes of detecting the trace component in high sensitivity, as will be described below. One is a method involving derivatization in which various reagents for derivatization are reacted with the objective components to convert into more readily detectable derivatives. The derivatization method in liquid chromatography is roughly classified into a pre-column labeling procedure in which derivatization is performed prior to separation with a separation column and a post-column labeling procedure in which derivatization is performed after separating into respective components using a separation column. Choice of either the pre-column labeling or the post-column labeling procedure upon derivatization depends on conditions of the reaction. As described in "ANALYSIS", February, 1987, pages 100–105, for example, in case that a rate of reacting with reagents for derivatization is slow or pressure must be applied, or, in case that gas generates or in case that interference in detection occurs with reagents for derivatization, etc., a modified pre-column labeling method is used; the modified method comprises performing derivatization of a sample in the system independently from an analyzer and performing separation and quantitative determination by liquid chromatography. On the other hand, in case that the reaction is not accompanied by the aforesaid problems, there is applied a pre-column labeling method in which a sample is injected into an analyzer and derivatization is conducted in a reaction coil to achieve separation and quantitative assay, or a post-column labeling method in which a reagent for derivatization is introduced into an analyzer after separation by liquid chromatography. In the post-column labeling method, great restrictions are imposed as compared to the pre-column labeling method because the reaction is caused in an eluate; however, the method has been widely adopted for biochemical analyzers mainly comprised of liquid chromatography such as an amino acid analyzer, a catecholamine analyzer, etc., since the method can be easily automated. Further, in the pre-column labeling method, reaction conditions can be set independently from conditions for analyzers and hence, a derivatization procedure coupled with a pretreatment or concentration is also utilized.

Apart from the trend that demands high sensitivity for detection of a trace component, development has also been extensively made on ultra high performance liquid chromatography using finely divided fillers or on micro liquid chromatography using a micro column. Effects attained by such analyzers are described in detail in J. Chromatogr. Library, "The Science of Chromatography", 32, 435-447 (1985). These ultra high performance liquid chromatography and micro liquid chromatography are considered to be one course of future liquid chromatography. To use a post-column labeling method in the case of assembling a biochemical analyzer by applying ultra high performance liquid chromatography or micro liquid chromatography leads to dilution of the objective components upon derivatization of the objective components and broadening peaks in detection or reduction in detection sensitivity due to noise in pulsation of a pump for feeding a reagent for derivatization, etc. thereby to sacrifice effects to be achieved by ultra high performance liquid chromatography and micro liquid chromatography. Standing on such a viewpoint, biochemical assay and an analyzer used for the assay have been investigated based on liquid chromatography adopting the pre-column labeling procedure to apply to analysis of amines, amino acids, aldehydes, etc. Among these methods, however, there are few methods in which objective components are converted into derivatives in a reaction coil of the analyzer system after a sample is injected into an analyzer, as shown in the "ANALYSIS" publication supra. This is because it takes a long time for derivatization of the objective components in a reaction coil, as compared to a time period required for separation and detection in liquid chromatography and therefore, in the case of treating many samples, it is advantageous to perform a derivatization step by a serial treatment outside the system, not in a reaction coil. Such biochemical assay is shown in J. Chromatogr., 344, 61–70 (1985) or Anal. Biochem., 155, 28–33 (1986). This assay is concerned with analysis of catecholamines with higher sensitivity in a simpler manner than in a conventional method; derivatization of catecholamines is performed outside the analyzer system, since it generally takes a time period as long a 40 minutes. On the other hand, a pre-column labeling method discussed in Anal. Biochem., 133, 330–335 (1983) is also known. In this case, pretreatment of a sample such as removal of protein from the sample, or the like is needed. In addition, it is difficult to uniformly mix the objective components in the sample with a reagent for derivatization.

In Published Examined Japanese Patent Application (KOKOKU) No. 62-56460, there is described liquid chromatography using a pre-column labeling apparatus used for derivatization of objective components which comprises introducing a sample into an adsorption column packed with a filler for adsorbing the objective components in the sample to adsorb the objective components onto the filler and then introducing a labeling agent into the adsorption column to convert the objective components into derivatives thereof. In this pre-column labeling apparatus, however, a rotary column is used as the adsorption column, its assembly is extremely complicated and a long period of time is required for analysis. Further the publication supra fails to disclose analysis of catecholamines.

As mentioned above, the prior art described above does not take into consideration shortening a time period for analysis including derivatization and improvement in accuracy of analysis. Further in the case that a derivatization reaction is serially performed for purposes of increasing the number of samples to be treated, a time period from the reaction to detection varies depending upon sample so that the prior art methods encounter the problem that analytical accuracy is lowered.

SUMMARY OF THE INVENTION

An object of the present invention is to provide a method for biochemical assay which provides high sensitivity and high accuracy without impairing characteristics of ultra high performance liquid chromatography and micro liquid chromatography.

Another object of the present invention is to provide a method for biochemical assay which enables to detection of catecholamines with high sensitivity in a short period of time.

A further object of the present invention is to provide an analyzer used for such a method for biochemical assay.

These and other objects of the present invention will be apparent from the following description.

In the first aspect of the present invention, there is provided a method for biochemical assay which comprises:

a first step of adjusting a specimen to prepare a sample;

a second step of introducing the sample into an adsorption column packed with an adsorbent and passing therethrough to adsorb objective components to the adsorption column;

a third step of introducing a reagent for derivatization to form derivatives of the objective components;

a fourth step of introducing a desorbing solution into the adsorption column to desorb the objective component derivatives retained in the adsorption column;

a fifth step of separating the objective component derivatives into respective components; and, a sixth step of detecting a concentration profile of each component separated to output this detection signal.

In the second aspect of the present invention, there is provided a method for biochemical assay which comprises:

a first step of adjusting a specimen to prepare a sample containing catecholamines;

a second step of introducing the sample into an adsorption column packed with an adsorbent and passing therethrough to adsorb the catecholamines to the adsorption column;

a third step of introducing a reagent for derivatization and a reaction accelerator to form catecholamine derivatives;

a fourth step of introducing a desorbing solution into the adsorption column to desorb the catecholamine derivatives retained in the adsorption column;

a fifth step of separating the catecholamine derivatives into respective components; and a sixth step of detecting a concentration profile of each component separated to output this detection signal.

In the third aspect of the present invention, there is provided an analyzer for biochemical assay equipped with a pump for supplying a sample, a separation column for separating objective components from the sample and a detector for detecting a concentration profile of each component in the eluate discharged from the separation column, wherein a fluid path changeover valve is provided in a fluid path connecting the pump and the separation column and the adsorption column packed with the adsorbent is connected via the fluid path changeover valve.

DETAILED DESCRIPTION OF THE INVENTION

Hereafter the present invention will be explained with respect to the first preferred embodiment by referring to FIGS. 1 through 5.

In this embodiment, the case of using a sample containing catecholamines as a sample is described but the sample is not deemed to be limited to catecholamines. The sample may be one containing amino acids, prostaglandins, polyamines etc.

Figure 1:
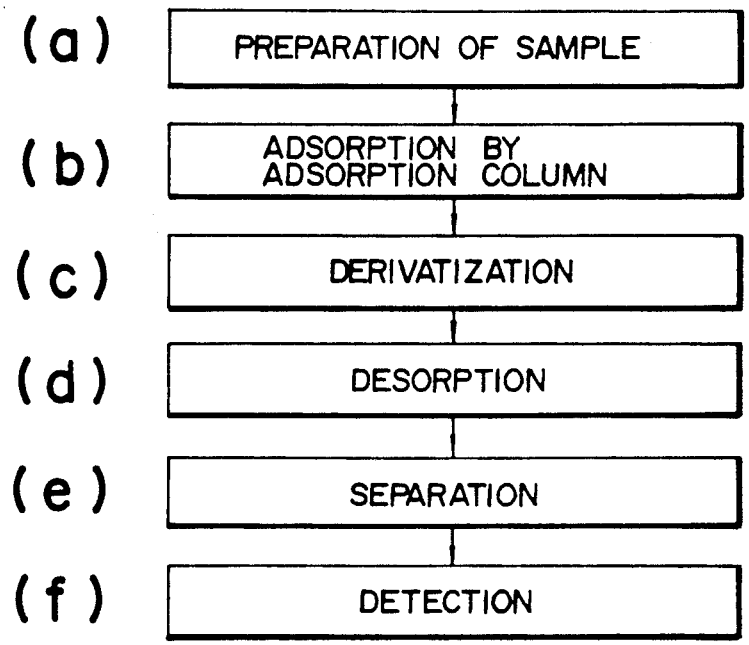
FIG. 1 is a flow chart showing an embodiment of the method for biochemical assay of the present invention.

At the first step denoted by (a) in FIG. 1, a specimen such as blood serum, urine, etc. is prepared into a sample after adjusting its pH to an appropriate value or mixing the specimen with a standard solution.

Next, at the second step denoted by (b) in FIG. 1, the sample is introduced into an adsorption column packed with an adsorbent and passed through the column. In this case, kind of the adsorbent and a liquid nature or ionic intensity of a carrier solution used to introduce the sample into the adsorption column are appropriately chosen thereby to selectively adsorb only catecholamines in the sample onto the adsorbent. As the adsorbent, an ion exchange resin, alumina, etc. are used. As the adsorption column, a multi-stage column such as a rotary column or the like is not particularly required but any ordinary single stage column may be employed.

Next, at the third step denoted by (c) in FIG. 1, a reagent for derivatization is introduced into the adsorption column and reacted with the catecholamines as the state of catecholamines adsorbed to the adsorbent is maintained. Thus, labeling is readily made to produce derivatives of the catecholamines.

As the reagent for derivatization, 1,2-diphenylethylenediamine is preferably used. Upon labeling, it is preferred to use a reaction accelerator. Typical examples of the reaction accelerator include salts of metal oxide such as ammonium molybdate, tungstenates, niobates, chromates, etc.; combination of nitrogen-containing compounds such as urea, hexamethylenetetramine, ammonium carbonate, etc. with zinc ions. Inter alia, the salts of metal oxide are particularly preferred. For labeling, an oxidizing agent such as potassium ferricyanide, etc. or an auxiliary reactant such as acetonitrile, etc. are generally used, together with these reagents.

By using the reaction accelerator described above, the labeling can be performed at a temperature of 30° C. or below in a shorter time period.

Then, at the fourth step denoted by (d) in FIG. 1, after a definite time for the labeling passed, if necessary and desired, the unreacted components or degraded components in the adsorption column are washed out and the objective component derivatives are desorbed from the adsorption column with a desorbing solution. It is desired that a regenerating solution is introduced into the adsorption column to completely remove globulin, etc. adsorbed to the adsorption column, prior to desorption of the objective component derivatives. A preferred example of the regenerating solution is an aqueous solution of neutral mineral salt such as sodium chloride, potassium chloride and magnesium chloride.

Next, at the fifth step shown by (e) in FIG. 1, the desorbed objective component derivative described above are introduced into the separation column provided in liquid chromatography (HPLC) to separate the objective component into the respective components. Then, at the sixth step shown by (f) in FIG. 1, concentration profile of each component separated by the separation column is detected by HPLC described above and the detection signal is output.

Figure 2:
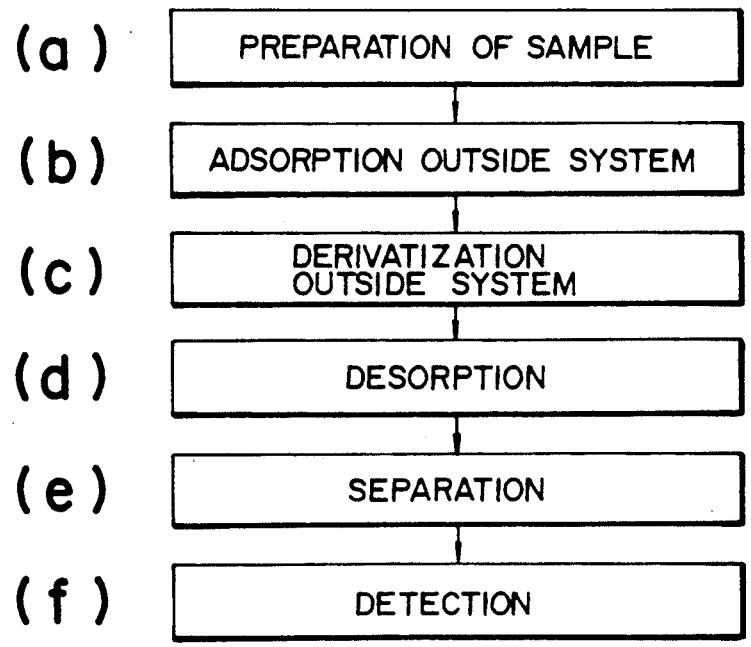
FIG. 2 is a flow chart showing an example of a method for biochemical assay according to the prior art.

In order to make the characteristics of this embodiment more clear, a method described in Anal. Biochem., 155, 28-23 (1986) is shown in FIG. 2 as an example of the prior art. In this example, the first step (a) in FIG. 2 is identical with the embodiment shown in FIG. 1 but the second step (b) through the fourth step (d) in FIG. 2 are performed in a test tube outside the analyzer system, not on an adsorption column. After separation by a separation column in liquid chromatography at the fifth step (e) in FIG. 2, concentration profile of each component is detected at the sixth step (f) in FIG. 2.

As is evident from FIG. 1, the embodiment attains effect of allowing to assay with high sensitivity owing to no requirement of diluting objective components and to subjecting whole sample and effect of preventing reduction in measurement accuracy due to scattering in reaction time caused by manual manipulation or degradation of the objective components by microorganism in the atomsphere. Further in this embodiment, the second and third steps are performed in the same adsorption column so that the embodiment is effective for shortening a time period for the labeling, improving accuracy in measurement, etc.

Figure 3:
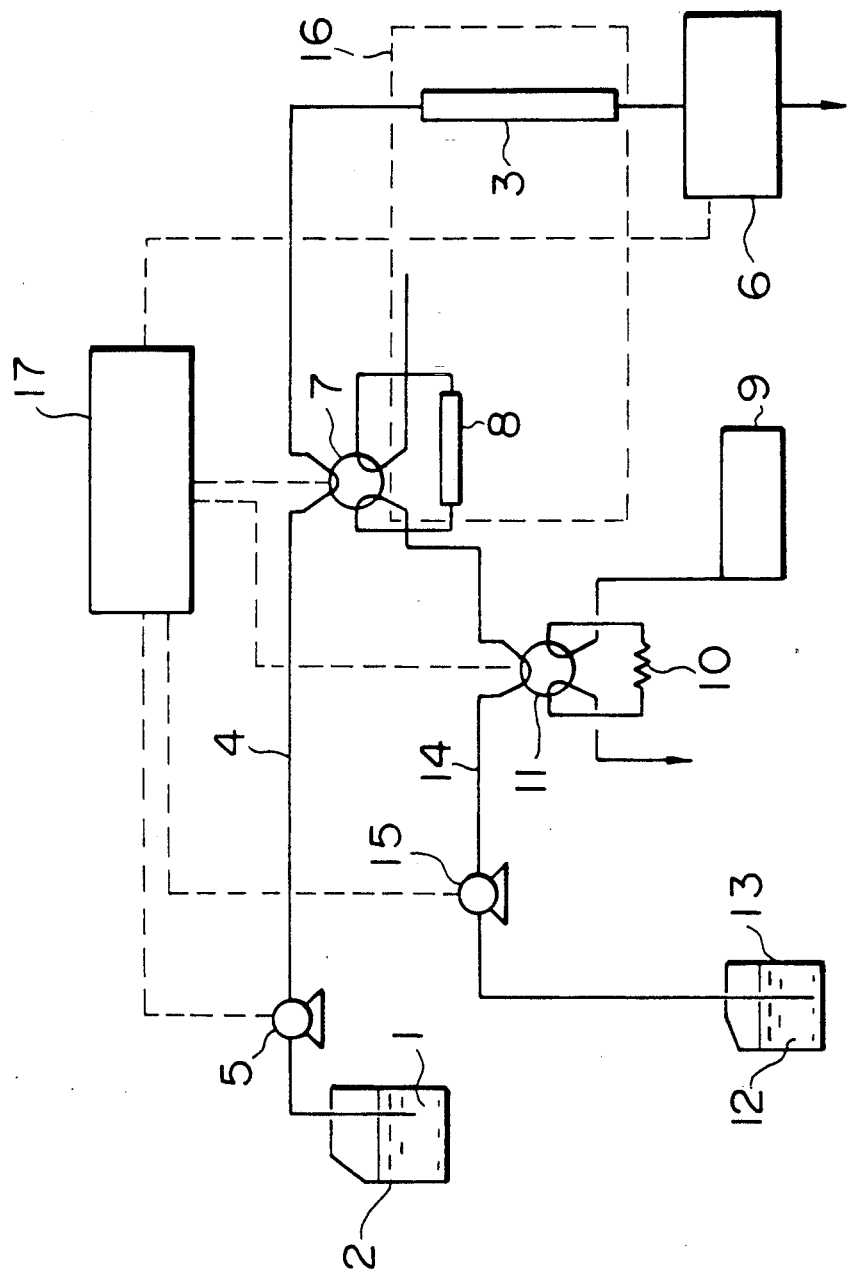
FIG. 3 shows a structure of an embodiment of an analyzer used for biochemical assay method of the present invention.

In FIG. 3, a preferred embodiment of an analyzer for the biochemical assay method of the present invention is shown. In the figure, high performance liquid chromatography is comprised of a container 2 packed with desorbing solution 1, a separation column 3, a fluid path 4 connecting the container 2 and the separation column 3, a feeding pump provided in the flow path and a detector 6. This separation column 3 is further connected via a fluid path changeover valve 7 with an autosampler for feeding a sample comprised of a turn table 9, a metering tube 10 and a fluid path changeover valve 11. In addition, a container 13 packed with an adjusting solution 12 is connected via a fluid path 14 with the separation column 3. A liquid-feeding pump 15 for feeding the adjusting solution 12 is provided between the fluid path changeover valve 11 and the container in the fluid path 14. An adsorption column 8 packed with an adsorbent is connected between the liquid feeding pump 15 and the separation column 3 via the fluid path changeover valve 7. The separation column 3 and the adsorption column 8 are encased in the same oven 16. Further the fluid path changeover valves 7 and 11, the liquid-feeding pumps 5 and 15, a column oven 16 and the detector 6 are connected with a controller 17, respectively. By this controller 17, timing for changeover of the fluid path changeover valves 7 and 11, a flow amount of the solution fed, temperature, wavelength and sensitivity can be controlled.

The adsorption column 8 is preferably encased in a thermostat or a container which is kept at a constant temperature. By doing so, a rate of the labeling can be controlled and the labeling can be performed at a temperature of 30° C. or lower. As the adsorption column, a multi-stage column such as a rotary column, etc. is not particularly required but any ordinary single stage column may be employed.

In this embodiment, the desorbing solution 1 is composed of, for example, acetonitrile, methanol and water [containing 0.01 M phosphate buffet (pH 7.0) and 0.1 M sodium dodecylsulfate] in 5:2:3 and the adjusting solution is composed of, for example, 0.01 M phosphate buffer (pH 5.8). Details of the constituent elements described above are as follows.

Adsorption column 8 ... Mitsubishi Chemical Industry Co., Ltd., CQK30S (acidic cation exchange resin), 40 mm I.D.×10 mm
Fluid path changeover valves 7 ... Rheodyne 600
Fluid path changeover valves 11 ... Rheodyne 7125 (equipped with an actuator driving apparatus)
Separation column 3 ... Hitachi Gel #3057 4 mm I.D.×150 nm
Oven 16 ... hand made
Fluid path changeover valve 11
Turn table 9
Metering tube 10 ... Hitachi 655A-40 automated sampler
Liquid-feeding pumps 5, 15 ... Hitachi L6000
Detector 6 ... Hitachi F-1000, Ex=350 nm, Em=485 nm
Controller 17 ... Hitachi L5000

Next, operation of a biochemical analyzer according to this embodiment will be explained below. The adjusting solution 12 is supplied to the adsorption column 8 packed with, for example, cation exchange resin, for example, in 1 ml/min, through the liquid-feeding pump 15 via the fluid path 14. A specimen such as blood serum, etc. is injected onto the adsorption column 8 as a sample coupled with the adjusting solution. In this case, the adsorbent in the adsorption column 8 is charged negatively and catecholamines in the serum positively so that adsorption occurs between both. On the other hand, for example, albumin in serum are charged negatively and thus eliminated from the system. In such a state that the catecholamines are adsorbed to the adsorption column 8, a reagent for derivatization is injected from the autosampler comprised of turn table 9, metering tube 10 and fluid path changeover valve 11 to react the reagent with the catecholamines in the adsorption column 8. In this case, the liquid-feeding pump 15 can be stopped or a feeding amount can be varied in order to control a reaction time. After a definite time period passed, the adsorption column 8 is washed with the adjusting solution 12 and the fluid path changeover valve 7 is switched over to pass the desorbing solution 1 through the adsorption column 8. The catecholamine derivatives are desorbed through the adsorption column 8 and enter into the separation column 3, where the derivatives are separated into the respective components. Concentration profile of each of these components is detected with detector 6.

Figure 4:
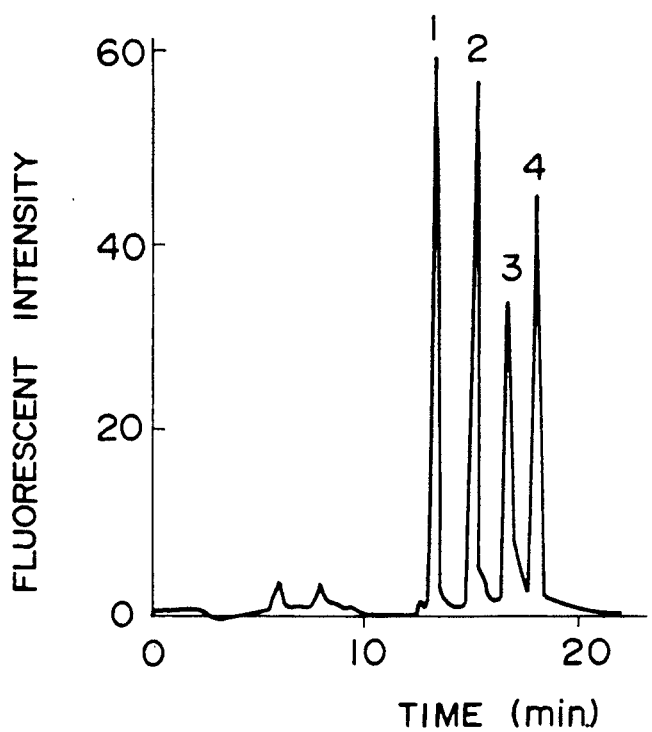
FIGS. 4 through 6 each shows chromatograms obtained using the analyzer of the present invention shown in FIG. 3.

FIG. 4 shows chromatograms in which blood serum is injected into the analyzer embodied above and detected using an adsorption column packed with an cation exchange resin and using 1,2-diphenylethylenediamine as a reagent for derivatization. The measurement was made in a chart speed of 10 mm/min with a fluorescence monitor sensitivity × 10 in a range of 10 mV. Peaks 1 to 4 correspond to the components shown below, respectively.

Peak 1:norepinephrine
Peak 2:epinephrine
Peak 3:dopamine
Peak 4:isoproterenol

According to the measurement results, it is understood that catecholamines are detected with high sensitivity.

Next, two experiments according to a method for biochemical assay and an analyzer by this embodiment are shown below.

EXPERIMENT 1

Figure 5:
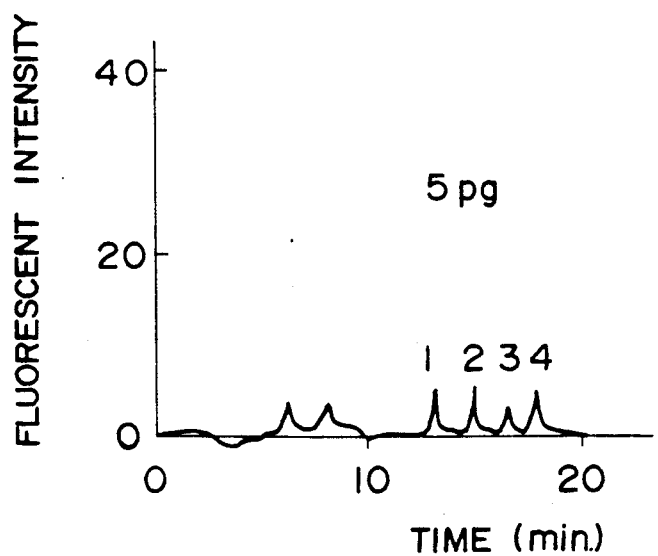

Using a sample obtained by adding catecholamines to model blood serum, the catecholamines were adsorbed in 5 pg to adsorption column 8, respectively and detected. The thus obtained chromatograms are shown in FIG. 5. Conditions are the same as in the embodiment described above.

EXPERIMENT 2

Analysis was performed as in the embodiment described above except that model blood serum having as close concentrations as 90 pg/ml epinophrine, 340 pg/ml norepinephrine and 50 pg/ml dopamine in normal blood was used and, reproducibility in measurement was examined. The results are shown in Table 1 below. In the table, values obtained by the prior art method shown in FIG. 2 are also presented in the table for purposes of comparison.

TABLE 1

| Component | Concentration (pg/ml) | Variation Coefficient (%) Experiment | Variation Coefficient (%) Prior art |
|---|---|---|---|
| Epinephrine | 90 | 1.6 | 7.0 |
| Norepinephrine | 340 | 1.4 | 7.0 |
| Dopamine | 50 | 1.7 | impossible to measure |

The values shown in Table 1 described above also include variation caused by concentrating operation with the adsorption column. From this table, it is noted that the measurement accuracy is higher in the cases in accordance with the present embodiment than in the prior art.

Next, the second preferred embodiment in which assay is performed, using a reaction accelerator coupled with the reagent for derivatization, with an analyzer equipped with an adsorption column encased in an oven maintained at a temperature of not higher than 30° C. will be explained.

As the reagent for derivatization containing a reaction accelerator, there was used a solution mixture of 10 mmoles of 1,2-diphenylethylenediamine (reagent for derivatization), 20 mmols of ammonium molybdate (reaction accelerator), 0.5 mmols of potassium ferricyanide (oxidizing agent) and 40% acetonitrile. The adsorption column was maintained at a temperature at 20° C. and the following assay was performed under the same conditions as in the embodiment described above.

Figure 6:
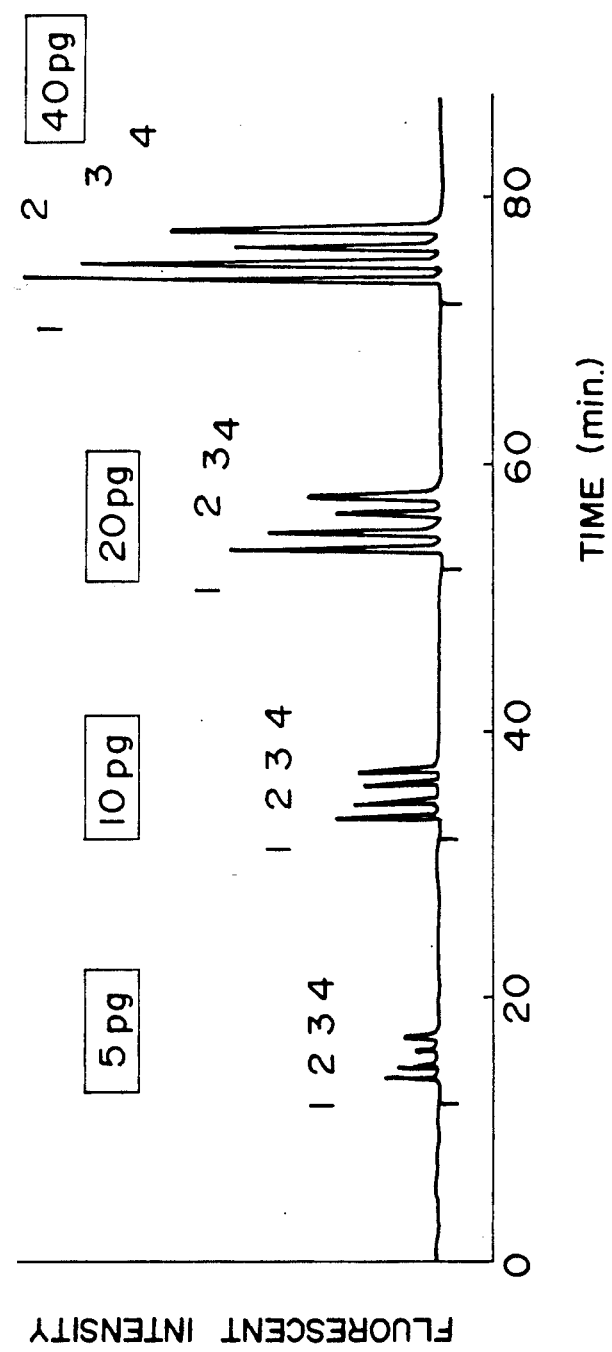

That is, a sample (1 ml) containing 5, 10, 20 or 40 pg of norepinephrine, epinephrine, dopamine and isoproterenol, respectively, was injected into the analyzer. The resulting chromatograms are shown in FIG. 6. Conditions were the same as in the embodiment described above, with a fluorescent monitor sensitivity × 10 in a recorder range of 10 mV in a chart speed of 10 mm/min. Peaks 1 to 4 are as shows.

Peak 1:norepinephrine
Peak 2:epinephrine
Peak 3:dopamine
Peak 4:isoproterenol

From FIG. 6, it is understood that catecholamines are detected with high sensitivity in a short period of time.

As described above, according to the present invention, the objective components such as catecholamines, etc. can be reacted with the reagent for derivatization after adsorption to the adsorption column and the temperature in the derivatization reaction can be controlled. Therefore, the present invention can provide effects of shortening a reaction time for the derivatization reaction, accurate control and improved accuracy in assay because of washing of impurities and unreacted components, etc.

While the invention has been described in detail and with reference to specific embodiments thereof, it is apparent to one skilled in the art that various changes and modifications can be made therein without departing from the spirit and the scope of the present invention.

What is claimed is:

1. A method for biochemical assay, comprising:
   providing a stationary, non-rotating single stage adsorption column packed with an adsorbent;
   introducing a sample into said adsorption column with an adjusting solution and passing said sample through said adsorption column to adsorb objective components on said adsorbent;
   providing a metering tube with a reagent for derivatization therein;
   introducing said reagent from said metering tube into said adsorption column with said adjusting solution to form derivatives of said objective components in said adsorption column;
   providing a separation column and a fluid path between said adsorption column and said separation column, and introducing a desorbing solution into said adsorption column to desorb said derivatives from said adsorption column and transfer said derivatives from said adsorption column to said separation column along said fluid path;
   separating said derivatives into respective components in said separating column; and
   detecting the separated components.

2. A method for biochemical assay of claim 1, wherein the temperature of said adsorption column is set to control a rate for the derivatization reaction of said objective components in the adsorption column.

3. A method for biochemical assay of claim 1, wherein said objective components in the sample are catecholamines.

4. A method for biochemical assay of claim 1, wherein a reaction accelerator is introduced into said adsorption column together with said reagent for derivatization.

5. A method for biochemical assay of claim 1, wherein a regenerating solution is introduced into said adsorption column after introducing said reagent and before introducing said desorbing solution.

6. A method for biochemical assay of claim 1, wherein a single stage column is used as said adsorption column, not a rotary column.

7. A method for biochemical assay of claim 1, wherein said adsorption column is maintained at a temperature not higher than 30° C.

8. A method for biochemical assay of claim 1 wherein said adsorption column and said separation column are provided within a single oven.

9. A method for biochemical assay of claim 1, wherein a regenerating solution is introduced into said adsorption column after introducing said reagent and before introducing said desorbing solution.

10. A method for biochemical assay of claim 9, wherein said regenerating solution is an aqueous solution of neutral mineral salt.

11. A method for biochemical assay, comprising:
providing an adsorption column packed with a negatively charged adsorbent;
introducing a sample containing catecholamines and albumin into said adsorption column with an adjusting solution and passing said sample through said adsorption column to adsorb said catecholamines on said negatively charged adsorbent, and discharging said albumin from said adsorption column;
providing a metering tube with a reagent for derivatization therein;
introducing said reagent from said metering tube into said adsorption column with said adjusting solution to form derivatives of said catecholamines in said adsorption column;
providing a separation column and a fluid path between said adsorption column and said separation column, and introducing a desorbing solution into said adsorption column to desorb said derivatives of catecholamine from said adsorption column and transfer said derivatives of catecholamine from said adsorption column to said separation column along said fluid path;
separating said derivatives of catecholamines into respective components in said separating column; and
detecting the separated components.

12. A method for biochemical assay of claim 11, wherein said adsorption column and said separation column are provided within a single oven.

13. A method for biochemical assay according to claim 11, wherein a reaction accelerator is introduced into said adsorption column with said reagent.

14. A method for biochemical assay of claim 13, wherein 1,2diphenylethylenediamine is used as said reagent for derivatization and a salt of metal oxide is used as said reaction accelerator.

15. A method for biochemical assay of claim 14, wherein said salt of metal oxide is a tungstate, a niobate or chromate.

* * * * *